United States Patent
Zhao et al.

(10) Patent No.: US 11,116,504 B2
(45) Date of Patent: Sep. 14, 2021

(54) ANASTOMOTIC/OCCLUSION REINFORCING AND REPAIRING COMPOSITE MEMBER AS WELL AS PREPARATION AND APPLICATION METHOD THEREOF

(71) Applicant: BEIJING BIOSIS HEALING BIOLOGICAL TECHNOLOGY CO., LTD., Beijing (CN)

(72) Inventors: Bo Zhao, Beijing (CN); Xuejun Li, Beijing (CN); Hongquan Wang, Beijing (CN); Yanrui Zhao, Beijing (CN); Fulei Fei, Beijing (CN); Jinhui Zhang, Beijing (CN); Dandan Sun, Beijing (CN)

(73) Assignee: BEIJING BIOSIS HEALING BIOLOGICAL TECHNOLOGY CO., LTD., Beijing (CN)

( * ) Notice: Subject to any disclaimer, the term of this patent is extended or adjusted under 35 U.S.C. 154(b) by 263 days.

(21) Appl. No.: 16/090,959

(22) PCT Filed: Nov. 30, 2017

(86) PCT No.: PCT/CN2017/113789
§ 371 (c)(1),
(2) Date: Oct. 3, 2018

(87) PCT Pub. No.: WO2018/121169
PCT Pub. Date: Jul. 5, 2018

(65) Prior Publication Data
US 2019/0125346 A1    May 2, 2019

(30) Foreign Application Priority Data
Dec. 26, 2016    (CN) .......................... 201611216405.4

(51) Int. Cl.
*A61B 17/072* (2006.01)
*A61B 17/115* (2006.01)
(Continued)

(52) U.S. Cl.
CPC .... *A61B 17/07292* (2013.01); *A61B 17/0466* (2013.01); *A61B 17/06166* (2013.01);
(Continued)

(58) Field of Classification Search
CPC ............ A61B 17/07292; A61B 17/115; A61B 17/12168; A61B 17/0466; A61L 31/14; A61L 31/146
See application file for complete search history.

(56) References Cited

U.S. PATENT DOCUMENTS

| | | | |
|---|---|---|---|
| 5,503,638 A | * | 4/1996 | Cooper ............ A61B 17/07207 606/148 |
| 5,769,892 A | | 6/1998 | Kingwell |

(Continued)

FOREIGN PATENT DOCUMENTS

| | | |
|---|---|---|
| CN | 1822865 | 8/2006 |
| CN | 103272278 | 9/2013 |

(Continued)

OTHER PUBLICATIONS

Tremblay et al., "A Comparison of Mechanical Properties of Materials Used in Aortic Arch Reconstruction," The Society of Thoracic Surgeons, 2009, pp. 1484-1491.

(Continued)

*Primary Examiner* — Anh T Dang
(74) *Attorney, Agent, or Firm* — Greenblum & Bernstein, P.L.C.

(57) ABSTRACT

The present disclosure relates to the technical field of medical equipment and discloses an anastomotic/occlusion reinforcing and repairing composite member which includes
(Continued)

a reinforcing and repairing portion, a protection portion and a connecting thread, wherein two ends of the reinforcing and repairing portion are detachably connected by the connecting thread; and the protection portion penetrates into a space enclosed by the two ends of the reinforcing and repairing portion. The present disclosure also provides a preparation and application method of the anastomotic/occlusion reinforcing and repairing composite member.

9 Claims, 4 Drawing Sheets

(51) Int. Cl.
*A61B 17/12* (2006.01)
*A61B 17/04* (2006.01)
*A61L 31/00* (2006.01)
*A61L 31/14* (2006.01)
*A61B 17/06* (2006.01)
*A61B 17/00* (2006.01)

(52) U.S. Cl.
CPC ...... *A61B 17/07207* (2013.01); *A61B 17/115* (2013.01); *A61B 17/1155* (2013.01); *A61B 17/12168* (2013.01); *A61L 31/005* (2013.01); *A61L 31/14* (2013.01); *A61L 31/146* (2013.01); *A61L 31/148* (2013.01); *A61B 2017/00004* (2013.01); *A61B 2017/00526* (2013.01); *A61B 2017/00831* (2013.01)

(56) References Cited

U.S. PATENT DOCUMENTS

| | | | | |
|---|---|---|---|---|
| 5,810,855 | A | * | 9/1998 | Rayburn .......... A61B 17/07207 227/176.1 |
| 5,814,057 | A | | 9/1998 | Oi et al. |
| 5,902,312 | A | * | 5/1999 | Frater .............. A61B 17/07207 606/148 |
| 6,063,097 | A | | 5/2000 | Oi et al. |
| 8,177,797 | B2 | | 5/2012 | Shimoji et al. |
| 8,956,390 | B2 | | 2/2015 | Shah et al. |
| 9,642,937 | B2 | | 5/2017 | Zhao et al. |
| 2004/0093029 | A1 | | 5/2004 | Zubik et al. |
| 2006/0178683 | A1 | | 8/2006 | Shimoji et al. |
| 2007/0049953 | A2 | | 3/2007 | Shimoji et al. |
| 2011/0087279 | A1 | | 4/2011 | Shah et al. |
| 2016/0101215 | A1 | | 4/2016 | Zhao et al. |

FOREIGN PATENT DOCUMENTS

| | | |
|---|---|---|
| CN | 106725679 | 5/2017 |
| EP | 0667119 | 8/1995 |
| WO | WO2009/143331 | 11/2009 |

OTHER PUBLICATIONS

Search Report from WIPO Patent Application No. PCT/CN2017/113789, dated Feb. 26, 2018, along with an English-language translation thereof.

\* cited by examiner

ANASTOMOTIC/OCCLUSION REINFORCING AND REPAIRING COMPOSITE MEMBER AS WELL AS PREPARATION AND APPLICATION METHOD THEREOF

TECHNICAL FIELD

The present disclosure relates to the technical field of medical equipment, and more particularly, to an anastomotic/occlusion reinforcing and repairing composite member as well as preparation and application method thereof.

BACKGROUND ART

Compared with the conventional surgery which starts with cutting by a scalpel/surgical scissors, the surgical reinforcing devices can reduce the risk of such surgical procedure to a large extent because they can quickly cut and close the tissues and organs in a patient's body at the same time and shorten the operation time, so the surgical reinforcing devices are widely used in surgery. The surgical reinforcing device usually has a jaw-like structure which usually comprises two separate arms, and the inner surface is the working surface. The first arm is preferably a cartridge arm having a cartridge surface comprising two or more staple lines, and the second arm is preferably an anvil arm having an anvil surface. The surgical reinforcing device may or may not have a cutting device with a cutting function.

In a typical anastomat surgery, two anastomotic arms are positioned in a pre-cut tissue and then tightly locked together. The user operates the stapler through an action process to synchronously complete stitching two or more staple lines to the tissue and forming a cut line in the middle of the suture. In this way, the operator can synchronously complete rapid suturing and cutting of the tissue. This procedure is much faster than using surgical scissors/scalpel to cut a tissue and suturing the incision with a seam in a conventional operation. The benefit of the anastomat surgery is that the bleeding time at the wound is reduced and the time for the entire operation is shortened, significantly improving the patient care.

In some operations, using bare staples directly, i.e., the anastomotic staples being in direct contact with the patient's tissue, is feasible, because before the healing, the patient's complete tissue can prevent the anastomotic staples from escaping from the tissue and compensate for the cracks. However, for some other operations, the tissue of the patient that needs to be sewed is so fragile that it is difficult to fix the anastomotic staples in place. For example, in lung surgery, some lung tissue with special lesions, which requires anastomosis, is very fragile. In extreme cases, an unprotected anastomotic seam is prone to be completely torn. With the increasing use of surgical reinforcing devices in the operations of diseased lung tissue, it has become increasingly important to take measures to protect the delicate tissue from being torn by the anastomotic staples or being torn during the surgical suture process. Furthermore, when the stapler is used, the leakage problem around the anastomotic staples also needs to be considered.

One known protective measure is use of reinforcing materials; that is, both the reinforcing material and the patient's tissue are used between the two arms of the stapler. Usually, first, the reinforcing material is applied to the arm of the surgical stapler in some manner, and then the surgical stapler is used for suturing to protect the patient's tissue.

Reinforcing materials clinically used in China are mainly synthetic materials (such as polypropylene, polylactic acid, etc.). However, biodegradable materials show obvious advantages because they are not permanent foreign matters. Among them, NEOVEIL made of polylactic acid material is the most prominent. However, these synthetic materials cannot help the healing of the wound (staple hole and cut surface).

The development direction of the modern medical implanted materials aims at biological materials that are degradable and can actively induce tissue regeneration. In recent years, a series of implanted materials derived from animal tissues or organs by decellularization and removal of immunogen, such as acellular pericardium, acellular dermal matrix, etc., have become popular, and they have the advantages of that they are degradable and low immunogenic and that they themselves and their degradant products all have good biocompatibility. Studies have found that extracellular matrix material (ECM) can provide a good microenvironment for tissue repair, and has the effect of inducing cell differentiation and promoting cell growth.

SUMMARY

The technical problem to be solved by the present disclosure is to provide an anastomotic/occlusion reinforcing and repairing composite member which can provide enough strength to the to-be-treated tissue to prevent suture tearing; and, with low or nearly no immunogenicity, the composite member realizes relatively low pathogenicity and high biocompatibility, while a large amount of beneficial compositions promoting tissue repairing are retained.

The technical solution adopted by the present disclosure is an anastomotic/occlusion reinforcing and repairing composite member including a reinforcing and repairing portion, a protection portion, and a connecting thread. The connecting thread detachably connects two ends of the reinforcing and repairing portion. The protection portion penetrates into a space enclosed by the two ends of the reinforcing and repairing portion.

The anastomotic/occlusion stoma may be a stomach anastomotic/occlusion stoma, an esophageal anastomotic/occlusion stoma, a duodenal anastomotic/occlusion stoma, a small intestinal anastomotic/occlusion stoma, a stump occlusion stoma after pneumonectomy, a bronchial stump anastomotic/occlusion stoma, a biliary tract anastomotic/occlusion stoma, a stump occlusion stoma after the pancreatectomy, a colorectal anastomotic/occlusion stoma, and a blood vessel anastomotic/occlusion stoma.

Preferably, the material of the reinforcing and repairing portion is non-immunogenic and can be degraded in vivo, has a three-dimensional mesh-like porous structure, can strengthen the anastomotic/occlusion stoma, and can be used together with a stapler/anastomat, or can also be a flaky antigen-deprived animal-derived extracellular matrix material including non-crosslinking collagen fiber, mucopolysaccharide, growth factor and glycoprotein. The collagen fiber is a composition comprising type I, type III, type IV and/or type VI collagen, the mucopolysaccharide is a composition comprising chondroitin sulfate and/or hyaluronic acid, and the growth factor is a composition comprising vascular endothelial growth factor, fibroblast growth factor and/or transforming growth factor. The antigen-deprived animal-derived extracellular matrix material is an antigen-deprived submucosa matrix material, a pericardium matrix material or a dermal matrix material or an antigen-deprived small intestinal submucosa matrix material, and the extracellular matrix material can be made from mammalian tissue and can be produced by risk treatment, immunogen removal, and/or sterilization.

The protection portion is a separating material disposed between the connecting thread and the reinforcing and repairing portion, for facilitating the loading of a stringed reinforcing and repairing sheet onto the arm of the stapler and protecting the braided mesh-like structure. Moreover, the protection portion at least partially separates the connecting thread from the arm of the anastomat to prevent the arm of the anastomat from tearing and damaging the connecting thread during assembly. Preferably, the protection portion is a planar sheet or a curved sheet, and the length of the protection portion may be greater than the length of the reinforcing and repairing portion, but at least a part thereof should be located in the space enclosed by the reinforcing and repairing portion. The part of the protection portion protruding out of the space enclosed by the reinforcing and repairing portion can facilitate manual withdrawal of the protection portion, and can also protect the connecting thread by bending to prevent abrasion of the connecting thread. The material of the protection portion can be one of the following: synthetic polymer material, ceramic material, metal material, Tyvek paper, and medical synthetic paper, or a combination of some of them. Preferably, the thickness of the protection portion is 50 to 10000 μm, preferably 100 to 600 μm or 300 to 350 μm.

The detachable connection specifically refers to that: at least one pair of holes is provided at corresponding positions along the edge of the two ends of the reinforcing and repairing portion, and each pair of holes includes thread holes respectively located at the two ends of the reinforcing and repairing portion. One single strand or strands of the connecting thread passes or pass through the thread holes to form a detachable braided mesh-like structure. Preferably, the material of the connecting thread is a medically usable thread; the connecting thread is woven into slipknots; the braided mesh-like structure is woven in the form of a slipknot; the braided mesh-like structure is woven in the manner of line, knot; the form of the slipknots includes continuous slipknots and interrupted slipknots; and the porosity of the braided mesh-like structure is 75 to 90%.

Preferably, the braided mesh-like structure is any of the following braided mesh-like structures.

The first type of braided mesh-like structure is divided in sequence into a first free section, n first half-open sections connected to one another, a pulling section, a holding section, a locking section, and a first release section from the starting end to the finishing end of the braid. The entire loop enclosed by each of the first half-open sections communicates two thread holes of a pair of holes. Open ends of the first half-open sections are located at the same end of the reinforcing and repairing portion. The locking section passes through the loops enclosed by the first half-open sections. From the starting end to the finishing end of the braid, an end of the first one of the first half-open sections at an opening, which is close to the starting end of the braid, is connected to the first free section; and an end of the n-th first half-open section at an opening, which is close to the finishing end of the braid, is connected to one end of the pulling section, and the other end of the pulling section is connected to one end of the holding section, and the other end of the holding section is connected to one end of the locking section, and the other end of the locking section is connected to the first release section.

The second type of braided mesh-like structure is divided in sequence into a second free section, n second half-open sections in series connection, and a second release section from the starting end to the finishing end of the braid. From the starting end to the finishing end of the braid, an end of the first one of the second half-open sections at an opening, which is close to the starting end of the braid, is connected to the second free section; and an end of the n-th one of the second half-open sections at an opening, which is close to the finishing end of the braid, is connected to the second release section. Each of the second half-open sections passes through the thread holes located at the same end of the reinforcing and repairing portion, and from the second one of the second half-open sections, the entire loop enclosed by each of the second half-open sections passes through the loop enclosed by the previous second half-open section.

The third type of braided mesh-like structure is divided in sequence into a third free section, 2n third half-open sections connected to one another, and a third release section from the starting end to the finishing end of the braid. From the starting end to the finishing end of the braid, an end of the first one of the third half-open sections at an opening, which is close to the starting end of the braid, is connected to the third free section; and an end of the 2n-th one of the third half-open sections at an opening, which is close to the finishing end of the braid, is connected to the third release section. The braided mesh-like structure is braided in a snakelike shape along the thread holes in the reinforcing and repairing portion. From the second one of the third half-open sections, the thread forming each third half-open section is interwoven with the loop enclosed by the previous third half-open section.

Compared with the prior art, the anastomotic/occlusion reinforcing and repairing composite member disclosed herein is advantageous in that it has low or nearly no immunogenicity, can avoid many immunological pathogenic reactions caused by the introduction of foreign cells, realizes relatively low pathogenicity and high biocompatibility, and maintains a large amount of beneficial compositions promoting tissue repairing.

The present disclosure also provides a preparation method of an anastomotic/occlusion reinforcing and repairing composite member. An anastomotic/occlusion reinforcing and repairing composite member obtained by this method is highly safe and convenient to use.

The technical solution adopted by the present disclosure is a method for preparing an anastomotic/occlusion reinforcing and repairing composite member, which comprises braiding the connecting thread on the reinforcing and repairing portion under aseptic conditions, and then attaching the protection portion, thereby obtaining the anastomotic/occlusion reinforcing and repairing composite member. The preparation method of the reinforcing and repairing portion may comprise the following steps:

(i) raw material selection and preliminary treatment: selecting small intestinal submucosa tissue material, removing lymphoid tissue, rinsing the material with water until no stain leaves on the surface, and filtering the material with a sieve:

(ii) risk treatment: soaking the small intestinal submucosa tissue filtered by the sieve in step (i) in peracetic acid-ethanol solution, and then filtering it with a sieve;

(iii) immunogen removal: mixing the small intestinal submucosa tissue which has gone through the risk treatment of step (ii) with a sodium chloride solution which has a concentration of 3-6 mol/L and a volume 20~30 times the volume of the small intestinal submucosa tissue which has gone through the risk treatment of step (ii); freezing the small intestinal submucosa tissue at −25~−20° C.; taking it out after 0.5~1.5 hours; placing it in a sodium chloride solution with the same concentration at a temperature of 35~40° C. for thawing; after repeating the freezing-thawing process for 3~5 times, rinsing off the sodium chloride; and filtering the tissue with a sieve:

(iv) fixation: selecting a specific mold with a needle base plate, a cover plate and a weight; laying the small intestinal submucosa tissue from which the immunogen has been removed in step (iii) on the needle base plate; covering it with the cover plate; squeezing it with the weight to allow water to overflow, obtaining a semi-finished product;

(v) vacuum freeze-drying: vacuum freeze-drying the semi-finished product; cutting the semi-finished product into a specific shape, obtaining the dry reinforcing and repairing portion;

(vi) sterilization and aeration: using ethylene oxide to sterilize the reinforcing and repairing portion of step (v), sterilization conditions: temperature: 35-40° C. temperature preservation time: 3.5 to 4.5 hours, humidity: 30 to 70%, concentration of ethylene oxide: 300~1000 mg/L, sterilization time: 3.5 to 4.5 hours: aerating the reinforcing and repairing portion in a ventilating aeration room, with the temperature being controlled between 15~25° C. for 10~20 days, to obtain a finished product of the reinforcing and repairing portion.

The sterilization method can also adopt radiation sterilization, dry heat sterilization, moist heat sterilization and/or gas sterilization.

Preferably, the volume concentration of peracetic acid in the peracetic acid-ethanol solution used in step (ii) is 0.1 to 5%, and the volume concentration of ethanol is 5 to 40%; the ratio of the volume of the peracetic acid-ethanol solution to the volume of a porcine small intestinal submucosa tissue is 20~40:1, the soaking time is 2~4 hours, and the temperature is 10~40° C.

Preferably, the cleaning in step (iii) comprises: using a PBS solution with a pH value of 6-8 and a volume 20-40 times the volume of the small intestinal submucosa tissue filtered by the sieve in step (ii) to ultrasonic clean the small intestinal submucosa tissue, with a washing temperature of 10~40° C. and a period of 10~30 minutes for each cleaning; repeatedly washing the tissue until the pH value of the mixed solution of the small intestinal submucosa tissue and the PBS solution is 6~8, obtaining the small intestinal submucosa tissue cleaned by the PBS solution; and then ultrasonic washing the small intestinal submucosa tissue with water for injection at a temperature of 10 to 40° C. until the detected conductivity of the mixed solution of the small intestinal submucosa tissue and the water for injection is 0 to 1 µS/cm.

Preferably, the vacuum freeze-drying conditions in step (v) are in sequence as follows: pre-freezing to −40~−50° C., preserving the temperature for 1~2 hours; adjusting the temperature to −10~−20° C., preserving the temperature for 5~7 hours; adjusting the temperature to −5~−4° C., preserving the temperature for 1.5~2.5 hours; adjusting the product temperature to 20~30° C.; and preserving the temperature for 3.5~4.5 hours.

Compared with the prior art, the preparation method of the anastomotic/occlusion reinforcing and repairing composite member in the present disclosure can not only provide sufficient strength for the tissue to be treated, achieving a longitudinal tensile strength of 24 N or more and a transverse tensile strength of 15 N or more and thus preventing the anastomotic/occlusion stoma from being torn, etc., but also make the assembly and use of the reinforcing material extremely easy and the reinforcing material not easy to fall off, which ensures the safety and stability of the surgical procedure. After the decellularization treatment in the preparation method, the extracellular matrix remains intact and continuous and has no cell residue, providing a good induction "template" and growth "soil" for cell differentiation and growth and providing a good basis for wound repair. The anastomotic/occlusion reinforcing and repairing composite member prepared by the method of the present disclosure has lower pathogenicity and higher biocompatibility, and retains a large amount of beneficial compositions that promote tissue repair.

The present disclosure also provides a simple method for using the anastomotic/occlusion reinforcing and repairing composite member. The anastomotic/occlusion reinforcing and repairing composite member is extremely simple to use and does not easily fall off, ensuring the safety and stability of the surgical procedure and improving the efficiency of surgery. The application method comprises the following steps: getting a reinforcing device which matches the anastomotic/occlusion reinforcing and repairing composite member; inserting a reinforcing portion of the reinforcing device into the space enclosed by the reinforcing and repairing portion; withdrawing the protection portion; pulling to tighten the connecting thread so that the reinforcing and repairing portion is fastened to the reinforcing portion of the reinforcing device; and after the stapling/anastomosing/suturing is completed, pulling and withdrawing the connecting thread.

Figure 1:
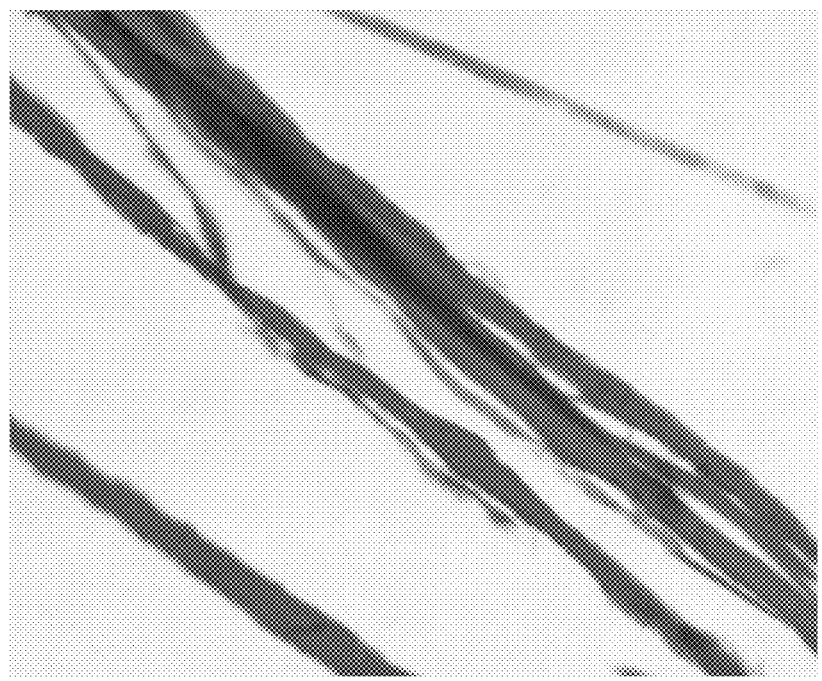
FIG. 1 is a HE staining section of the reinforcing and repairing sheet of the present disclosure.
Figure 2:
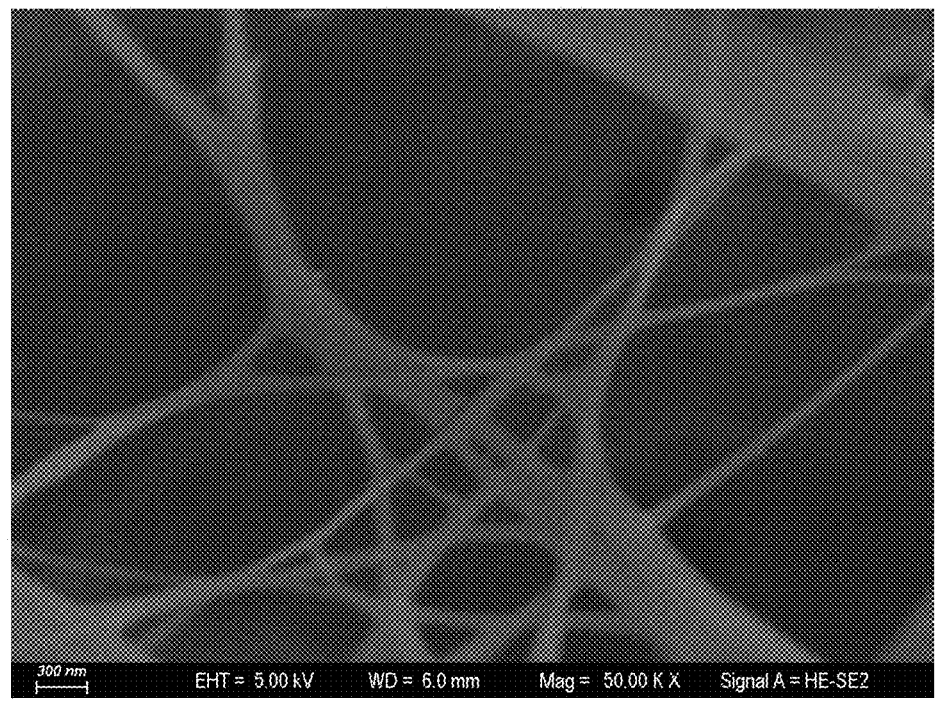
FIG. 2 is a SEM photograph of the reinforcing and repairing sheet of the present disclosure.
Figure 3:
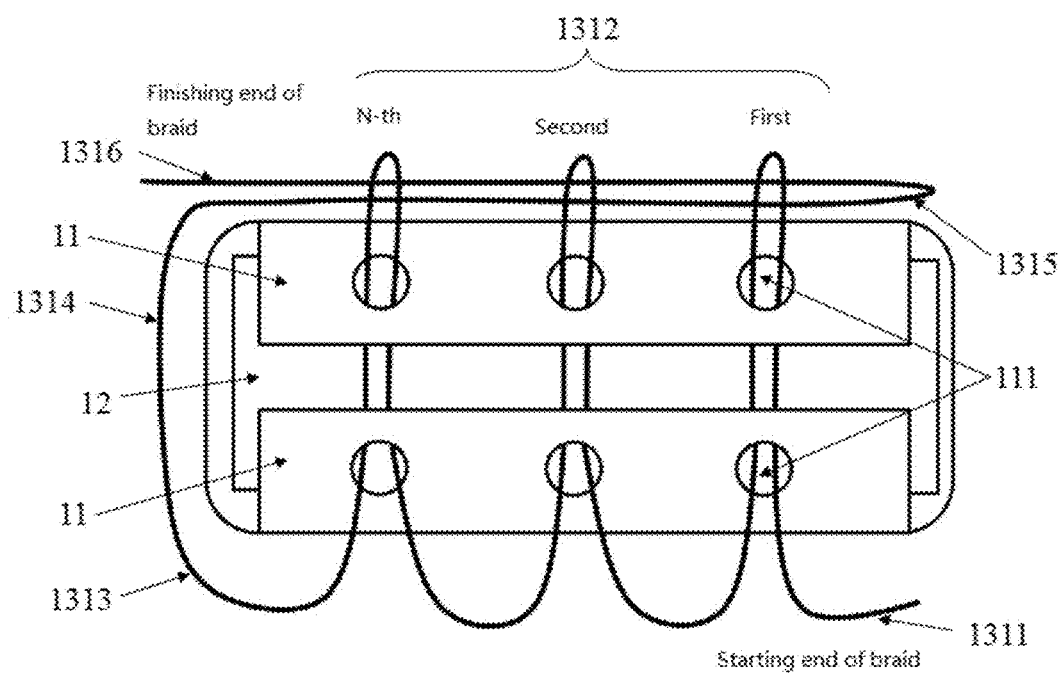
FIG. 3 is a schematic top view of a first embodiment of the anastomotic/occlusion reinforcing and repairing composite member of the present disclosure.
Figure 4:
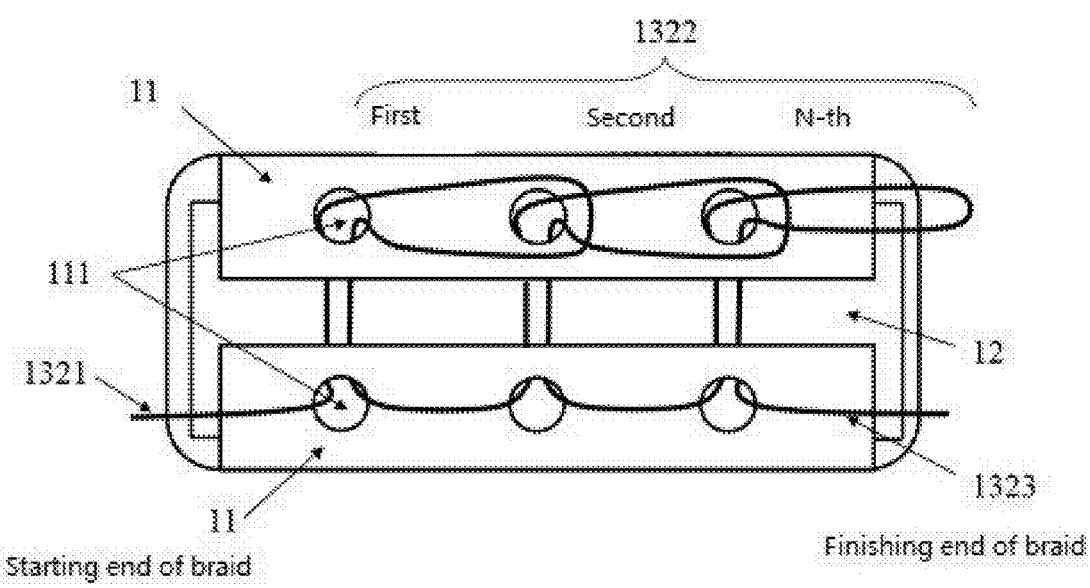
FIG. 4 is a schematic top view of a second embodiment of the anastomotic-occlusion reinforcing and repairing composite member of the present disclosure.
Figure 5:
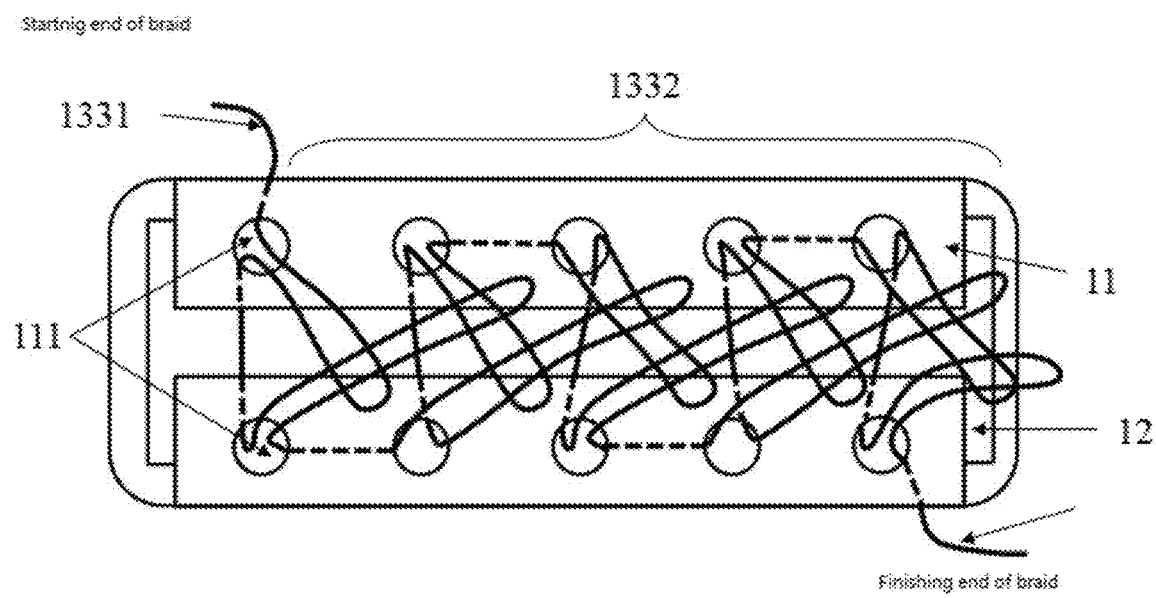
FIG. 5 is a schematic top view of a third embodiment of the anastomotic/occlusion reinforcing and repairing composite member of the present disclosure.
Figure 6:
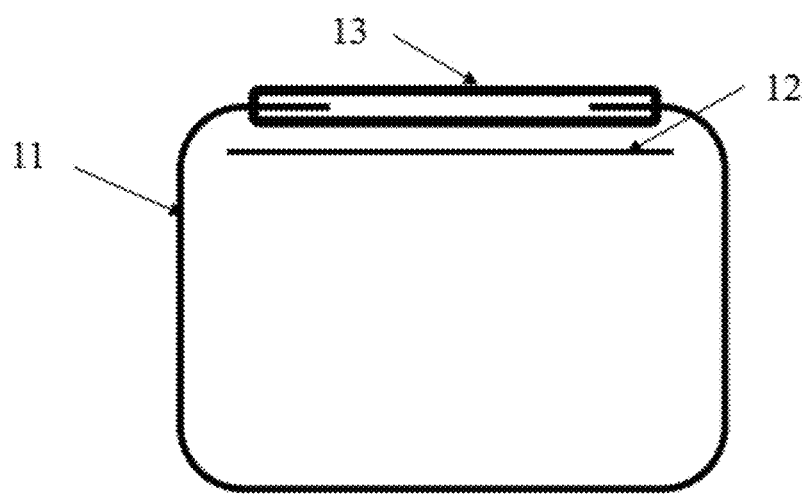
FIG. 6 is a schematic side view of the anastomotic/occlusion reinforcing and repairing composite member of the present disclosure.
Figure 7:
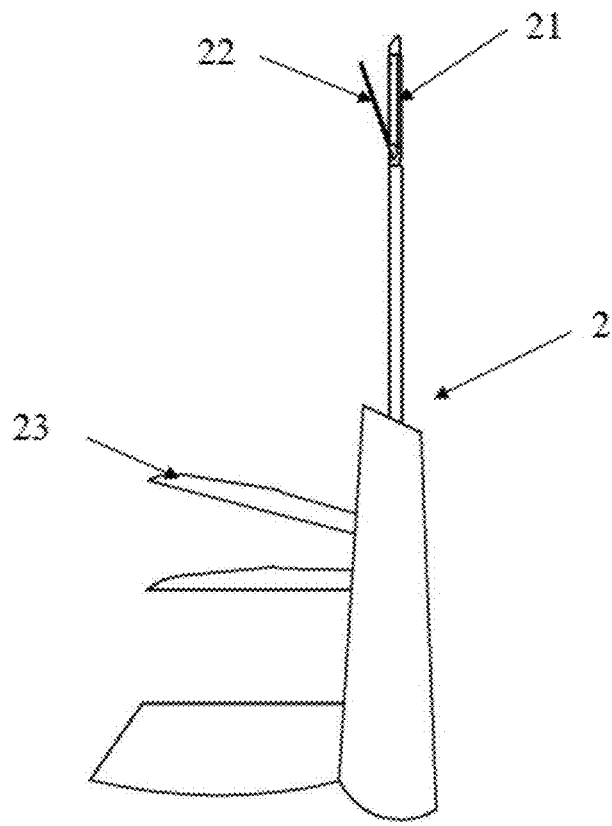
FIG. 7 is a schematic view of a stapler of a surgical reinforcing device.
Figure 8:
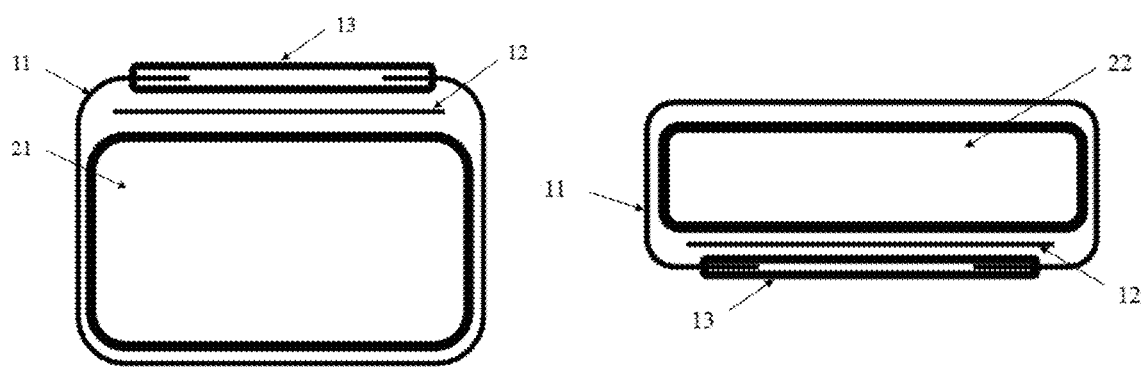
FIG. 8 is a side view showing that the anastomotic/occlusion reinforcing and repairing composite member of the present disclosure is attached to an anvil arm and a cartridge arm of the stapler of the surgical reinforcing device.

11. reinforcing and repairing portion; 12. protection portion; 13. connecting thread; 111. pairs of holes; 1311. first free section; 1312. first half-open section; 1313. pulling section; 1314. holding section; 1315. locking section; 1316. first release section; 1321. second free section; 1322. second half-open section; 1323. second release section; 1331. third free section; 1332. third half-open section; 1333. third release section; 2. stapler; 21. anvil arm; 22. cartridge arm; 23. handle

DETAILED DESCRIPTION OF EXAMPLES

The present disclosure provides an anastomotic/occlusion reinforcing and repairing composite member as well as preparation and application method thereof. In order to help understand various aspects of the present disclosure, the following examples are provided. It should be noted that the examples are for explaining the present disclosure, and the present disclosure is not limited by these examples. The raw material can be obtained from pigs or cattle, and the pigs can be pigs having a homozygote rate of 50% or more. The following description takes pig as an example.

Example 1

Preparation of the Reinforcing and Repairing Sheet

It should be noted that the reinforcing and repairing sheet is one of the finished products of the reinforcing and repairing portion commonly used in the present disclosure.

The reinforcing and repairing sheet can be prepared in the way below.

(a) Selection and preliminary treatment of the raw material: The Chinese inbred line Wuzhishan mini-pig is selected as the animal source. The animal species is determined using the method specified in patent ZL200510008994.2. The small intestinal tissue of the freshly slaughtered Chinese inbred line Wuzhishan mini-pig is cleaned, and the small intestinal submucosa tissue is separated and is divided into a required size, and the lymphatic tissue is removed, and the small intestinal submucosa tissue is rinsed with tap water for 1~3 times, and then is rinsed with purified water until the surface has no stains, and the rinsed small intestinal submucosa tissue is left unmoved and filtered with a sieve.

(b) Risk treatment: The small intestinal submucosa tissue filtered in step (a) is soaked in a peracetic acid-ethanol solution. This process can be performed in a stainless steel barrel. The concentration of peracetic acid is 0.1 to 5%, the concentration of ethanol is 5~40%, the inactivation time is 2~4 hours, the ratio of the volume of the solution to the volume of the small intestinal submucosa tissue is 20~40:1, the temperature range is 10~40° C., and the small intestinal submucosa tissue is filtered by a sieve.

(c) Immunogen removal: The small intestinal submucosa tissue which has been treated in step (b) is put in a sodium chloride solution with a concentration of 4 mol/L, and the ratio of the volume of the sodium chloride solution to the volume of the small intestinal submucosa tissue after the treatment in step (b) is 20~30:1. Freeze the small intestinal submucosa tissue at −20° C. and take it out after about 1 hour, and then place it in a sodium chloride solution with the same concentration at a temperature of 37° C. for thawing. Repeat the freezing-thawing process for 3 to 5 times, and then wash the small intestinal submucosa tissue in purified water with ultrasonic wave. Rinse off the sodium chloride and filter the small intestinal submucosa tissue with a sieve.

(d) Washing process: Wash the small intestinal submucosa tissue using a PBS solution with a pH value of 6~8, a temperature of 10~40° C. and a volume 20~40 times the volume of the small intestinal submucosa tissue treated in step (c), for a period of 10~30 minutes each time. Repeat washing the tissue for 2~4 times until the pH value is 6~8; and then wash the small intestinal submucosa tissue with water for injection at a temperature of 10 to 40° C. until the detected conductivity of the mixed solution of the small intestinal submucosa tissue and the water for injection is below 1 S/cm. The ratio of the volume of the water for injection to the volume of a porcine small intestinal submucosa tissue is 20~40:1. The washing process needs to be conducted in an ultrasonic wave washing machine.

(e) Fixation: This step is performed on a mold. The mold consists of three parts: a needle base plate, a cover plate and a weight. It is necessary to select different molds according to different sizes, and the small intestinal submucosa tissue is laid on the needle base plate. The product is covered with an impermeable stainless steel cover plate. The area of the cover plate is the size of the final cut or wider. A weight of 5~10 kilograms is placed on the stainless steel cover plate so that the water overflows under pressure from the perimeter. Layers of half-pressed small intestinal submucosa tissue are superimposed on each other to ensure tight adhesion between the upper and lower layers, obtaining a semi-finished reinforcing and repairing sheet.

(f) Vacuum freeze-drying: This process needs to be carried out in a vacuum freeze dryer. The freeze-drying process of semi-finished products needs to be reconfirmed according to different equipment. The mold is laid in a vacuum freeze dryer, the door of the freeze-drying chamber is closed, and the circulation pump is started to work for about 1 minute, and the compressor is turned on to freeze the freeze-drying box. Pre-freeze the product to −45° C., preserve this temperature for about 1~2 hours, turn on the vacuum pump, adjust the product temperature to about −15° C. to sublimate. About 5~7 hours later, adjust the product temperature to 0° C. and preserve this temperature for 2 hours. Adjust the product temperature to 25° C. and preserve this temperature for 4 hours. The vacuum freeze-drying process is completed, and the dried reinforcing and repairing sheet is obtained.

(g) Forming: After the dried product is taken out, it is cut into a fixed shape. The connecting thread is assembled or sewed onto the dry product. Tyvek paper of an appropriate size is added. For insurance, a double-layer Tyvek packaging bag is used for packaging. The process requires sterile transfer and handling.

(h) Sterilization and aeration: The product is sterilized with ethylene oxide. Sterilization conditions: temperature: 40° C., temperature preservation time: 4 hours, humidity: 30 to 70%, concentration of ethylene oxide: 300 to 1000 mg/L, sterilization time: 4 hours, aerating process: in a ventilated aeration chamber, the temperature is controlled at 20° C. and the time period is about 14 days, and a finished product of the reinforcing and repairing sheet is obtained.

The sterilization methods can also use radiation sterilization, dry heat sterilization, moist heat sterilization and/or gas sterilization.

Example 2

Effect Verification Experiment of the Reinforcing and Repairing Sheet of the Present Disclosure Preferably, the degradation time in vivo is 1 to 3 months. The mechanical properties of the reinforcing and repairing sheet include burst strength, suture retention, and/or tensile strength. FIG. 1 shows a HE staining section of the reinforcing and repairing sheet. According to FIG. 1, after HE staining, when the sample in Example 1 is observed by an optical microscope, it is found that the extracellular matrix is retained in a complete and continuous manner and no cell residue, according to the preparation method provided in the present disclosure.

By observing the sample with a scanning electron microscope, it can be seen that the extracellular matrix of the small intestinal submucosa tissue obtained after the treatment and the collagen fibers are intact, undamaged and free from breakage, and form a kind of interlaced porous network structure. It is proved by researches that the structure can provide a good induction "template" and growth "soil" for cell differentiation and growth and provide a good basis for wound repair.

The physicochemical properties of the sample in Example 1 are further examined. The examined items include pH, heavy metal content and residue on ignition, suture tensile strength, and tensile strength.

a. pH: Prepare a sample according to Example 1. Examine pH according to the method specified in 5.4.1 of GB/T 14233.1-2008, the difference between the pH of the sample test solution and the pH of the blank control solution does not exceed 1;

b. Heavy metal content: Prepare a sample according to Example 1. The content of lead and chromium is tested according to the atomic absorption spectrophotometer method prescribed in 5.9.1 of GB/T 14233.1-2008, and the content of mercury and arsenic is tested according to the atomic fluorescence spectrometry method prescribed in 5.9.3 of GB/T 14233.1-2008. The results show that the heavy metal content is less than 0.1 μg/g;

c. Residue on ignition: Prepare a sample according to Example 1. Measure the percentage of the residue on ignition according to the method specified in 0841 of the "Pharmacopoeia of the People's Republic of China" (four volumes, the edition of the year of 2015), showing that the residue on ignition is 1.0%:

d. Suture tensile strength: Prepare a sample according to Example 1. In a position 2 mm from the edge of one end of the reinforcing and repairing sheet, suture a 3-0 non-absorbable suture thread, fix the other end of the reinforcing and repairing sheet and the suture thread respectively on the tensile meter, pull the reinforcing and repairing sheet at a rate of 20 mm/min until the suture site is torn, and record the maximum force value. The result shows that the maximum value of the reinforcing and repairing sheet prepared by the method of the present disclosure is ION or more;

e. Tensile strength: Prepare a sample according to Example 1. Cut the sample into a size of 2 cm×5 cm, and conduct a test after the sample is placed in a condition of relative humidity of 40%-60% and a temperature of 22° C.±2° C. for 2 hours. Fix both ends of the sample on the chucks of a tensile tester and pull the sample outwards at a rate of 100 mm/min until the sample breaks. The longitudinal test and the transverse test are conducted respectively. The final results show that the longitudinal tensile strength can reach 24N or more, and the transverse tensile strength can reach 15N or more.

A biochemical test is performed on the reinforcing and repairing sheet.

a. Bacterial endotoxin test: Prepare a sample according to Example 1. Perform the test according to the method specified in GB/T 14233.2-2005. The result shows that bacterial endotoxin is less than 2 EU/g.

b. Cell residue examination: Three products are taken for HE staining. Three visual fields are selected for each section. Observe the number of intact cells with a 400× optical microscope and then divide the number by 3. The results show that the average number of intact cells in each field is 0. It is sufficient to avoid immune pathogenic reactions caused by the introduction of foreign cells.

c. DNA residue: Prepare a sample according to Example 1. According to the method specified in 3407 of "Pharmacopoeia of the People's Republic of China" (four volumes, the edition of the year of 2015), the amount of DNA remaining in the sample provided in Example 1 is measured by a fluorescent staining method. The results show that the amount of DNA remaining in the sample is less than 10 μg/g. Various inflammatory reactions caused by the acceptor's immune response to the animal's DNA are greatly reduced, or even because the amount of DNA residue is so low that no obvious inflammatory response is found.

d. α-Gal clearance: Prepare a sample according to Example 1. Detect the α-Gal clearance according to the method specified in "Part 5: Determination of α-Gal Antigen Clearance in Animal Derived Medical Equipment Using M86 Antibody, Immunogenicity Evaluation Method for Medical Equipment". The result shows that the α-Gal clearance rate is 99.4% e. IgA Residue: Prepare samples according to Example 1. Take 10 samples, sampling, extraction, and detect the IgA residue using a porcine immunoglobulin A (IgA) quantitative detection kit (ELISA). The results show that the IgA residue of the sample is less than 1 μg/g, which indicates that the sample has low or no immunogenicity.

f. FGF-2 retention: Prepare samples according to Example 1. Take 10 samples, sampling, extraction, and detect the FGF-2 content using a porcine basic fibroblast growth factor (FGF2) assay kit. The results show that the average retention amount of the FGF-2 of the samples is 30.8 ng/g±17.3 ng/g.

g. VEGF retention: Prepare samples according to Example 1. Take 10 samples, sampling, extraction, and detect VEGF content using a porcine vascular endothelial growth factor (VEGF) kit. The results show that the average retention amount of VEGF of the samples is 99.6 ng/g±2.4 ng/g.

h. Hyaluronic acid (HA) retention: Prepare samples according to Example 1. Take 10 samples, sampling, extraction, and detect hyaluronic acid (HA) content using a hyaluronic acid detection kit. The results show that the average retention amount of hyaluronic acid (HA) of the samples is 332 μg/g±231 μg/g.

i. Retention of glucosamine sulfate (sGAGs): Prepare samples according to Example 1. Take 10 samples, sampling, extraction, and detect the content of glucosamine sulfate (sGAGs) using a Biocolor's glucosamine sulfate detection Kit. The results show that the average content of glucosamine sulfate (sGAGs) in the samples is 7442 μg/g±6393 μg/g.

The results of the biological tests indicate that the reinforcing and repairing sheet of the present disclosure has low pathogenicity and high biocompatibility, and retains a large amount of beneficial compositions that promote tissue repair.

For the biological evaluation of the anastomotic reinforcing and repairing sheet, the detected items include cytotoxicity, delayed-type hypersensitivity reaction, and intradermal reaction.

a. Cytotoxicity (MTT method): Prepare samples according to Example 1. Sampling, extraction (Referring to GB/T 16886.12, the extraction proportion is chosen to be 6 cm²/mL, the extraction medium is complete cell culture medium, and the extraction conditions are 37° C. 24 h). In accordance with the method specified in GB/T 16886.5-2003 (Part 5: "In Vitro Cytotoxicity Test" of "Biological Evaluation of Medical Equipment"), it is detected that the cytotoxicity is less than or equal to 1st grade.

b. Delayed-type hypersensitivity reaction: Prepare samples according to Example 1. Sampling. Carry out the detection in accordance with the delayed-type hypersensitivity reaction closed application method specified in GB/T 16886.10-2003 (Part 10: "Stimulation and Delayed-type Hypersensitivity Action Test" of "Biological Evaluation of Medical Equipment"). An extract liquid is selected for the test sample (Physiological saline is chosen for the polar extraction medium and cottonseed oil is chosen for the non-polar extraction medium. The extraction ratio is selected to be 6 cm$^2$/mL and the extraction conditions are 37° C. and 72 h.). The results show no delayed-type hypersensitivity reaction.

c. Stimulation: Prepare samples according to Example 1. Sampling. Carry out the detection in accordance with the intradermal reaction method specified in GB/T 16886.10-2003 (Part 10: "Stimulation and Delayed-type Hypersensitivity Action Test" of "Biological Evaluation of Medical Equipment"). Physiological saline is chosen for the polar extraction medium and cottonseed oil is chosen for the non-polar extraction medium. The extraction ratio is selected to be 6 cm$^2$/mL and the extraction conditions are 37° C. and 72 h. The results show that the difference of comprehensive average score between the test sample and the solvent is not greater than 1.0.

An in vitro simulation of the degradation process of the anastomotic reinforcing and repairing sheet is described. Samples are prepared according to Example 1. Control the sterilization parameters in the ethylene oxide sterilization step so that the sterilization time is 4 h, 5 h, 6 h, 7 h, and 8 h, respectively. A sample of 10 mg is taken from each group of the samples obtained (cut into strips). Place them in a PBS solution of 2 mL containing a proteinase K of 0.2 mg/mL and place them in a water bath at 56° C. Take a photo every 15 minutes and record the material degradation process until all the material is dissolved without solid body residue. Results show that the in vitro simulated degradation time of the samples of which the sterilization time are 4 h, 5 h, 6 h, 7 h and 8 h are 120 min, 90 min, 75 min, 60 min and 45 min, respectively.

Angiogenic effect and examination of the reinforcing and repairing sheet are described. Six samples prepared in Example 1 are used as the test group, and six "BARD" patches which are commercial wound repair materials are used as the control group. The samples prepared in Example 1 are sterilized with low-temperature ethylene oxide prior to use, and the BARD patches have been sterilized and aseptically transported. Twelve blocks of a size of 1×1.5 cm are taken from the twelve samples and are implanted into rats' subcutaneousness. After 3 weeks, the angiogenic effect of each sample is quantitatively evaluated by microvascular fluorography. Three implants of the BARD patches and three implants of the samples according to the present disclosure are infused with gelatin ink, and the blood vessel volumes in the samples are quantitatively measured by calculating the diameter, density, and area of the blood vessels in the samples. The other three BARD implants and the other three implants of the samples according to the present disclosure go through histological studies with sections and H&E staining method to characterize cell growth.

The results of microvascular fluorography show that all implants have angiogenic effect. The blood vessel growth of BARD is significantly lower than that of the patches according to the present disclosure, and the blood vessel ingrowth is observed only in one of the six implants studied. The results of the blood vessel volume studies show that the vessel volume of the BARD implants is much lower than that of the test group. The results of histological studies are also consistent with the results of microvascular fluorography and gelatin ink infusion. The test group has significant fibrovascular ingrowth and shows notable evidence effect of functional reconstruction; whereas only a very small amount of fibrovascular ingrowth is observed in the BARD implants of the control group.

The three types of the braided mesh-like structure anastomotic/occlusion reinforcing and repairing composite member of the present disclosure and the application method thereof will be further described with reference to the appended drawings.

Example 3

The first type of braided mesh-like structure is divided in sequence into a first free section 1311, a plurality of first half-open sections 1312 connected to one another, a pulling section 1313, a holding section 1314, a locking section 1315, and a first release section 1316, from the starting end to the finishing end of the braid. The number of the first half-open sections 1312 may be the same as the number of the pairs of the holes 111. The entire loop enclosed by each of the first half-open sections 1312 communicates two thread holes of a pair of holes 111. Open ends of the first half-open sections 1312 are located at the same end of the reinforcing and repairing portion 11. The locking section 1315 passes through the loops enclosed by the first half-open sections 1312. From the starting end to the finishing end of the braid, an end of the first one of the first half-open sections 1312 at an opening, which is close to the starting end of the braid, is connected to the first free section 1311; and an end of the last one of the first half-open sections 1312 at an opening, which is close to the finishing end of the braid, is connected to one end of the pulling section 1313, and the other end of the pulling section 1313 is connected to one end of the holding section 1314, and the other end of the holding section 1314 is connected to one end of the locking section 1315, and the other end of the locking section 1315 is connected to the first release section 1316.

After the connecting thread 13 is braided according to the first type of braided mesh-like structure, the protection portion 12 is inserted into the space enclosed by the two ends of the reinforcing and repairing portion 11 to constitute an anastomotic/occlusion reinforcing and repairing composite member in a loose state of the connecting thread 13. Sleeve the anvil arm 21 and/or the cartridge arm 22 of the stapler 2 with the anastomotic/occlusion reinforcing and repairing composite member in a loose state, and locate the braided mesh-like structure and the protection portion 12 which fits to the braided mesh-like structure on the non-working surface of the anvil arm 21 and/or the cartridge arm 22, and withdraw the protection portion 12. Then, while the first free section 1311, the holding section 1314, and the first release section 1316 are remained unmoved, the pulling section 1313 is pulled to fasten the anastomotic/occlusion reinforcing and repairing composite member to the anvil arm 21 and/or to the cartridge arm 22, so that the first release section 1316 is located near the handle 23 of the stapler 2, and the stapler 2 having a reinforcing and repairing function is used to perform a stapling/anastomosing/suturing operation. After the stapling/anastomosing/suturing operation is completed, the first release section 1316 is pulled to withdraw the connecting thread 13.

Example 4

The second type of braided mesh-like structure is divided in sequence into a second free section 1321, n second half-open sections 1322 in series connection, and a second release section 1323, from the starting end to the finishing end of the braid. The number of the second half-open sections 1322 may be the same as the number of the pairs of the holes 111. From the starting end to the finishing end of the braid, an end of the first one of the second half-open sections 1322 at an opening, which is close to the starting end of the braid, is connected to the second free section 1321; and an end of the n-th one of the second half-open sections 1322 at an opening, which is close to the finishing end of the braid, is connected to the second release section 1323. Each of the second half-open sections 1322 passes through the thread holes located at the same end of the reinforcing and repairing portion 1, and from the second one of the second half-open sections, the entire loop enclosed by each of the second half-open sections 1322 passes through the loop enclosed by the previous second half-open section 1322.

After the connecting thread 13 is braided according to the second type of braided mesh-like structure, the protection portion 12 is inserted into the space enclosed by the two ends of the reinforcing and repairing portion 11 to constitute an anastomotic/occlusion reinforcing and repairing composite member in a loose state of the connecting thread 13. Sleeve the anvil arm 21 and/or the cartridge arm 22 of the stapler 2 with the anastomotic/occlusion reinforcing and repairing composite member in a loose state, and locate the braided mesh-like structure and the protection portion 12 which fits to the braided mesh-like structure on the non-working surface of the anvil arm 21 and/or the cartridge arm 22, and withdraw the protection portion 12. Then, while the second free section 1321 and the second release section 1323 are remained unmoved, the loop enclosed by the n-th one of the second half-open sections 1322 is pulled to fasten the anastomotic/occlusion reinforcing and repairing composite member to the anvil arm 21 and/or to the cartridge arm 22, so that the second release section 1323 is located near the handle 23 of the stapler 2, and the stapler 2 having a reinforcing and repairing function is used to perform a stapling/anastomosing/suturing operation. After the stapling/anastomosing/suturing operation is completed, the second release section 1323 is pulled to withdraw the connecting thread 13.

Example 5

The third type of braided mesh-like structure is divided in sequence into a third free section 1331, 2n third half-open sections 1332 connected to one another, and a third release section 1333, from the starting end to the finishing end of the braid. The number of the third half-open sections 1332 may be twice the number of the pairs of the holes 111. From the starting end to the finishing end of the braid, an end of the first one of the third half-open sections 1332 at an opening, which is close to the starting end of the braid, is connected to the third free section 1331; and an end of the 2n-th one of the third half-open sections 1332 at an opening, which is close to the finishing end of the braid, is connected to the third release section 1333. The braided mesh-like structure is braided in a snakelike shape along the thread holes in the reinforcing and repairing portion 11. From the second one of the third half-open sections, the thread forming each third half-open section 1332 is interwoven with the loop enclosed by the previous third half-open section 1332.

After the connecting thread 13 is braided according to the third type of braided mesh-like structure, the protection portion 12 is inserted into the space enclosed by the two ends of the reinforcing and repairing portion 11 to constitute an anastomotic/occlusion reinforcing and repairing composite member in a loose state of the connecting thread 13. Sleeve the anvil arm 21 and/or the cartridge arm 22 of the stapler 2 with the anastomotic/occlusion reinforcing and repairing composite member in a loose state, and locate the braided mesh-like structure and the protection portion 12 which fits to the braided mesh-like structure on the non-working surface of the anvil arm 21 and/or the cartridge arm 22, and withdraw the protection portion 12. Then, while the third free section 1331 and the third release section 1333 are remained unmoved, the loop enclosed by the 2n-th one of the third half-open sections 1332 is pulled to fasten the anastomotic/occlusion reinforcing and repairing composite member to the anvil arm 21 and/or to the cartridge arm 22, so that the third release section 1333 is located near the handle 23 of the stapler 2, and the stapler 2 having a reinforcing and repairing function is used to perform an stapling/anastomosing/suturing operation. After the stapling/anastomosing/suturing operation is completed, the third release section 1333 is pulled to withdraw the connecting thread 13.

The examples of the present disclosure take a stapler commonly used in surgeries as an example to explain the present disclosure. Staples commonly used in a stapler in surgeries are made of titanium, magnesium, aluminum or other absorbable materials. The composite member may also be applied to other types of stapler/anastomat such as linear staplers/anastomats and circular staplers/anastomats.

It is understood that the braided mesh-like structures in the embodiments/examples and the appended drawings of the present disclosure are for illustrative purposes only, and in actual practice the braided mesh-like structure may also take other forms such as having more line holes or more hole pairs on each side according to the actual length and the fastening strength of the anastomotic/occlusion reinforcing and repairing composite member and the characteristics of the mating stapler/anastomat/suturing device.

Although the present disclosure has been described above by way of the preferred embodiments, the preferred embodiments shall not be construed as restricting the claims. The present disclosure is not limited to the embodiments/examples, and the specific structure of the present disclosure is allowed to vary. It should be obvious that various modifications implemented within the protection scopes of the independent claims are covered by the protection scope of the present disclosure.

The invention claimed is:

1. An anastomotic/occlusion reinforcing and repairing composite member configured for arrangement upon an anastomat, wherein the anastomotic/occlusion reinforcing and repairing composite member comprises:
   a reinforcing and repairing portion,
   a connecting thread forming a detachable connection, which detachably connects two ends of the reinforcing and repairing portion, and
   a protection portion which penetrates into a space enclosed by the two ends of the reinforcing and repairing portion,
   wherein the protection portion is arranged and operable to prevent contact between the connecting thread and the anastomat while the composite member is arranged upon the anastomat,
   wherein the detachable connection specifically refers to that: at least a number n pair of holes is provided at corresponding positions along each edge of the two ends of the reinforcing and repairing portion, and each pair of holes includes thread holes respectively located at the two ends of the reinforcing and repairing portion, and one single strand or strands of the connecting thread passes or pass through the thread holes to form a detachable braided mesh-like structure, and wherein the braided mesh-like structure is any of the following braided mesh-like structures:

a first type of braided mesh-like structure having a first braid, which is divided in sequence into a first free section, a number n of first half-open sections connected to one another, a first pulling section, a first holding section, a first locking section, and a first release section from a starting end to a finishing end of the first braid; wherein each of the first half-open sections forms a respective loop that communicates with two thread holes of a pair of holes of the at least number n pair of holes; wherein open ends of the first half-open sections are located at a same end of the reinforcing and repairing portion; wherein the first locking section passes through the respective loops formed by the first half-open sections; wherein from the starting end to the finishing end of the first braid, an end of a first one of the first half-open sections at an opening, which is close to the starting end of the first braid, is connected to the first free section, and an end of an n-th one of the first half-open sections at an opening, which is close to the finishing end of the first braid, is connected to one end of the first pulling section, and the other end of the first pulling section is connected to one end of the first holding section, and the other end of the first holding section is connected to one end of the first locking section, and the other end of the first locking section is connected to the first release section;

a second type of braided mesh-like structure having a second braid, which is divided in sequence into a second free section, a number n of second half-open sections in series connection, and a second release section from a starting end to a finishing end of the second braid; wherein from the starting end to the finishing end of the second braid, an end of a first one of the second half-open sections at an opening, which is close to the starting end of the second braid, is connected to the second free section, and an end of an n-th one of the second half-open sections at an opening, which is close to the finishing end of the second braid, is connected to the second release section; wherein each of the second half-open sections passes through the thread holes located at the same end of the reinforcing and repairing portion, and wherein from a second one of the second half-open sections, an entire loop formed by each of the respective second half-open sections passes through a loop formed by a previous second half-open section; and a third type of braided mesh-like structure having a third braid, which is divided in sequence into a third free section, a number 2n third half-open sections connected to one another, and a third release section from a starting end to a finishing end of the third braid; wherein from the starting end to the finishing end of the third braid, an end of a first one of the third half-open sections at an opening, which is close to the starting end of the third braid, is connected to the third free section, and an end of a 2n-th one of the third half-open sections at an opening, which is close to the finishing end of the third braid, is connected to the third release section; wherein the third type of braided mesh-like structure is braided in a snake-like shape along the thread holes in the reinforcing and repairing portion; wherein from a second one of the third half-open sections, a thread forming each third half-open section is interwoven with a loop formed by a previous third half-open section.

2. The anastomotic/occlusion reinforcing and repairing composite member according to claim 1, wherein a material of the reinforcing and repairing portion is non-immunogenic and degradable in vivo; a material of the protection portion is one of a synthetic polymer material, ceramic material, metal material, non-woven polyethylene sheet material paper, and medical synthetic paper, or a combination of some of them; and a material of the connecting thread is a medically usable thread.

3. The anastomotic/occlusion reinforcing and repairing composite member according to claim 1, wherein the protection portion is a planar sheet or a curved sheet, a thickness of the protection portion is 50 to 10000 μm, and a length of the protection portion is greater than a length of the reinforcing and repairing portion.

4. A method of preparing the anastomotic/occlusion reinforcing and repairing composite member according to claim 1, comprising braiding the connecting thread on the reinforcing and repairing portion under aseptic conditions, and then attaching the protection portion, thereby obtaining the anastomotic/occlusion reinforcing and repairing composite member, wherein the preparation method of the reinforcing and repairing portion comprises the following steps:

(i) raw material selection and preliminary treatment: selecting small intestinal submucosa tissue material, removing lymphoid tissue, rinsing the material with water until no stain leaves on the surface, and filtering the material with a sieve;

(ii) risk treatment: soaking the small intestinal submucosa tissue filtered by the sieve in step (i) in peracetic acid-ethanol solution, and then filtering it with a sieve;

(iii) immunogen removal: mixing the small intestinal submucosa tissue which has gone through the risk treatment of step (ii) with a sodium chloride solution which has a concentration of 3-6 mol/L and a volume 20~30 times the volume of the small intestinal submucosa tissue which has gone through the risk treatment of step (ii); freezing the small intestinal submucosa tissue at −25~−20° C.; taking it out after 0.5~1.5 hours; placing it in a sodium chloride solution with the same concentration at a temperature of 35~40° C. for thawing; after repeating the freezing-thawing process for 3~5 times, rinsing off the sodium chloride;

(iv) fixation: selecting a specific mold with a needle base plate, a cover plate and a weight; laying the small intestinal submucosa tissue from which the immunogen has been removed in step (iii) on the needle base plate; covering it with the cover plate; squeezing it with the weight to allow water to overflow, obtaining a semi-finished product;

(v) vacuum freeze-drying: vacuum freeze-drying the semi-finished product; cutting the semi-finished product into a specific shape, obtaining a dry reinforcing and repairing portion;

(vi) sterilization and aeration: using ethylene oxide to sterilize the reinforcing and repairing portion of step (v) under the following sterilization conditions: temperature: 35-40° C., temperature preservation time: 3.5 to 4.5 hours, humidity: 30 to 70%, concentration of ethylene oxide: 300~1000 mg/L, sterilization time: 3.5 to 4.5 hours; aerating the reinforcing and repairing portion in a ventilating aeration room, with the temperature being controlled between 15~25° C. for 10~20 days, to obtain a finished product of the reinforcing and repairing portion.

5. The method of preparing the anastomotic/occlusion reinforcing and repairing composite member according to claim 4, wherein a volume concentration of peracetic acid in the peracetic acid-ethanol solution used in step (ii) is 0.1 to 5%, and a volume concentration of ethanol is 5 to 40%; a ratio of the volume of the peracetic acid-ethanol solution to the volume of the small intestinal submucosa tissue is 20~40:1, a soaking time is 2~4 hours, and a temperature is 10~40° C.

6. The method of preparing the anastomotic/occlusion reinforcing and repairing composite member according to claim 4, wherein the cleaning in step (iii) to rinse off the sodium chloride comprises: using a PBS solution with a pH value of 6-8 and a volume 20-40 times the volume of the small intestinal submucosa tissue filtered by the sieve in step (ii) to ultrasonic clean the small intestinal submucosa tissue, with a washing temperature of 10~40° C. and a period of 10~30 minutes for each cleaning; repeatedly washing the tissue until the pH value of the mixed solution of the small intestinal submucosa tissue and the PBS solution is 6~8, obtaining the small intestinal submucosa tissue cleaned by the PBS solution; and then ultrasonic washing the small intestinal submucosa tissue with water for injection at a temperature of 10 to 40° C. until a detected conductivity of the mixed solution of the small intestinal submucosa tissue and the water for injection is 0 to 10 μS/cm.

7. The method of preparing the anastomotic/occlusion reinforcing and repairing composite member according to claim 4, wherein vacuum freeze-drying conditions in step (v) are in sequence as follows: pre-freezing to −40~−50° C., preserving the temperature for 1~2 hours; adjusting the temperature to −10~−20° C., preserving the temperature for 5~7 hours; adjusting the temperature to −5~−4° C., preserving the temperature for 1.5~2.5 hours; adjusting the product temperature to 20~30° C., and preserving the temperature for 3.5~4.5 hours.

8. The method of preparing the anastomotic/occlusion reinforcing and repairing composite member according to claim 4, wherein the small intestinal submucosa tissue is a small intestinal submucosa tissue of a pig.

9. A method of applying the anastomotic/occlusion reinforcing and repairing composite member according to claim 1, wherein the method comprises the following steps: getting a reinforcing device which matches the anastomotic/occlusion reinforcing and repairing composite member; inserting a reinforcing portion of the reinforcing device into a space enclosed by the reinforcing and repairing portion; withdrawing the protection portion; pulling to tighten the connecting thread so that the reinforcing and repairing portion is fastened to the reinforcing portion of the reinforcing device; and after the stapling/anastomosing/suturing is completed, pulling and withdrawing the connecting thread.

* * * * *